United States Patent [19]
Welker

[11] Patent Number: 5,303,599
[45] Date of Patent: Apr. 19, 1994

[54] MINIATURIZED SAMPLER

[75] Inventor: Brian H. Welker, Sugar Land, Tex.

[73] Assignee: Welker Engineering Company, Sugar Land, Tex.

[21] Appl. No.: 922,032

[22] Filed: Jul. 29, 1992

[51] Int. Cl.$^5$ .............................................. G01N 1/14
[52] U.S. Cl. ...................................... 73/863.84
[58] Field of Search ........... 73/863.83, 863.84, 864.34, 73/864.35; 92/102; 417/379

[56] References Cited

U.S. PATENT DOCUMENTS

| | | | |
|---|---|---|---|
| 1,352,288 | 9/1920 | Bras | 92/102 |
| 2,764,996 | 10/1956 | Brown | 92/102 |
| 3,093,086 | 6/1963 | Altoz et al. | 92/102 |
| 3,229,527 | 1/1966 | Johnson | 73/863.84 |
| 3,321,977 | 5/1967 | Topham | 73/863.84 |
| 4,440,032 | 4/1984 | Welker | 73/863.84 |
| 4,531,895 | 7/1985 | Zeck | 417/401 |
| 4,928,536 | 5/1990 | Welker | 73/863.83 |

FOREIGN PATENT DOCUMENTS 2103572  1/1972  Fed. Rep. of Germany ........ 92/102

OTHER PUBLICATIONS

Welker, Welker Engineering Company, Inline Relief and Sampler Head Assemblies, P.O. Box 1228, Bellaire, Tex.

Primary Examiner—Robert Raevis
Attorney, Agent, or Firm—Lawrence E. Evans, Jr.

[57] ABSTRACT

The miniaturized sampler is activated by a diaphragm motor that can be screwed together by hand. The sampler uses an elastomeric collection head and typically takes a small sample each time the diaphragm motor is activated. The collection head is connected to a piston by a pin and ring arrangement that can be economically manufactured and easily serviced. Because the collection head is smaller than prior art designs, it takes less force to activate. A smaller collection head can be driven by a smaller diaphragm motor which allows overall sampler size and weight to be reduced when compared with prior art designs.

9 Claims, 10 Drawing Sheets

MINIATURIZED SAMPLER

BACKGROUND OF THE INVENTION

1. Field of the Invention

The instant invention relates to a device for sampling gases and more particularly to a device for periodically taking samples of natural gas from a natural gas pipeline and for passing the samples to a means for storing the gas for later analysis.

2. Description of Related Art

Natural gas typically occurs as a mixture of low molecular weight hydrocarbons obtained in petroleum-bearing regions throughout the world. In the United States, it occurs chiefly in the southwestern states and Alaska. Natural gas is composed primarily of methane. It may also include ethane, propane, isobutane, butane, pentane and hexane which are sometimes referred to as "light liquids," because they may exist in liquid or gas phase, depending on pressure and temperature. Natural gas may also include nitrogen, water, hydrogen sulfide and other fluids.

The content of natural gas varies widely from location to location. Some gas wells produce primarily methane and are referred to in the industry as "dry wells." These wells produce hydrocarbons in commercial quantities and should not be confused with the term "dry hole." A well which is incapable of producing hydrocarbons in commercial quantities is called a "dry hole"; it is typically capped and written off as a loss. Some gas wells produce methane in combination with "light liquids" and perhaps other fluids and are referred to in the industry as "wet wells." The natural gas produced from "dry wells" and "wet wells" is commingled in gathering systems and transmission pipelines. Extraction plants are often located between gathering systems and transmission lines to strip out the "light liquids" and other fluids. Depending on supplies and prices, the extraction plant may or may not be in operation.

Today, natural gas is bought and sold based on volume and heating value. The amount of heat generated by the burning gas is measured in Btu's (British thermal units). Gas from "wet wells" produces more energy in the form of Btu's per volume when burned than does gas from a "dry well." For example, methane, by itself, produces approximately 900 Btu's when burned. If a little ethane is mixed with the methane, the heating value rises to approximately 1000 Btu's. In general, the natural gas industry strives to deliver approximately 1000 Btu gas; however, the heating value can vary significantly, depending on the types and amounts of the "light liquids" present in the natural gas. As a result, both buyers and sellers of natural gas are interested in the heating value, expressed as Btu content, of the gas in order to insure that a fair price is paid for the gas.

The price of natural gas in most industrial applications is based on volume which is adjusted either up or down, based on a Btu factor. Today, it is also common practice for many local utilities to sell natural gas to homeowners based on volume which is adjusted based on a Btu factor. These heating value adjustments are based on actual tests of the natural gas. These tests typically require that samples of the gas be taken in the field and brought to a laboratory for analysis. The heating value of natural gas is typically analyzed with a calorimeter.

Figure 1:
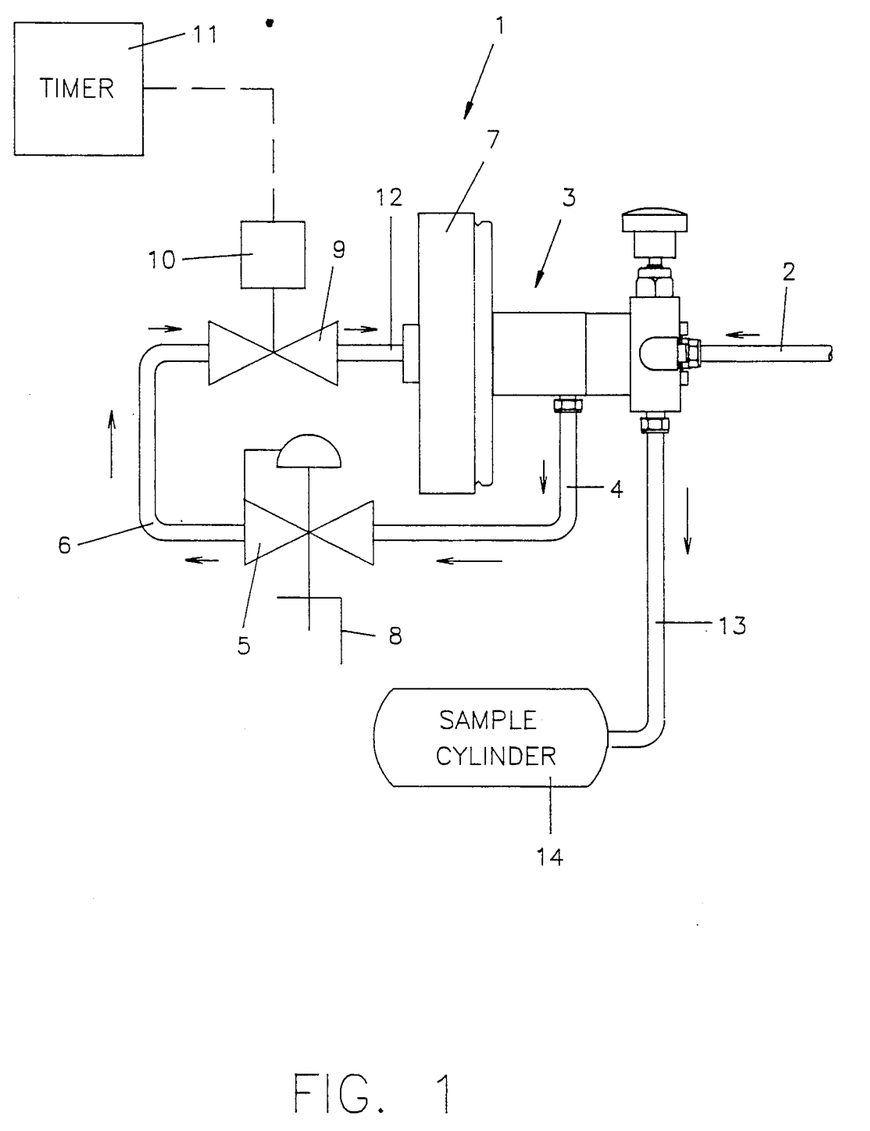
FIG. 1 is a schematic drawing of a natural gas sampler system of the present invention.

In order to analyze the heating value of the natural gas in a pipeline, sampler systems, such as that shown in FIG. 1, have been developed. FIG. 1 is a schematic of the present invention with ancillary operating equipment attached. As shown in FIG. 1, natural gas from a pipeline passes from the pipeline (not shown) to the sampler assembly, generally labeled 1, through an inlet pipe 2. Inlet pipe 2 is connected to a sample pump 3. The natural gas entering sample pump 3 through inlet pipe 2 enters sample pump 3 at the natural gas pipeline pressure. This pipeline pressure varies from a low of about 100 pounds per square inch ("psi") to higher than 1800 psi but is typically about 1100 psi.

A portion of the natural gas from inlet pipe 2 passes through sample pump 3 and exits sample pump 3 through outlet pipe 4. Outlet pipe 4 is connected to regulator/relief valve 5. Regulator/relief valve 5 drops the natural gas pressure from outlet pipe 4, which is at pipeline pressure, to a value of about 60–70 psi and passes the natural gas under the reduced pressure out of regulator/relief valve 5 through connecting pipe 6. The regulator/relief valve 5 includes a relief valve to vent excessive pressures to the atmosphere.

Connecting pipe 6 connects regulator/relief valve 5 to timing valve 9. Timing valve 9 is opened and closed by a solenoid 10 that is in turn controlled by a timer 11. Timer 11 may be a simple device that periodically activates solenoid 10 to open and close timing valve 9. However, the preferred form of timer 11 is a device that reacts to the volume of gas passing through the natural gas pipeline to activate solenoid 10 to open and close timing valve 9 so that periodic samples, corresponding to the flow rate through the pipeline, are taken by sample pump 3.

When timing valve 9 is opened under the direction of solenoid 10, natural gas flows through the inlet pipe 2, the sample pump 3, the outlet pipe 4 to the regulator relief valve 5 from connecting pipe 6 through timing valve 9 through sample pump pipe 12 to diaphragm motor 7 of sample pump 3. When, under the direction of solenoid 10 and timer 11, timing valve 9 is closed, timing valve 9 is vented to the atmosphere so that natural gas under pressure in the diaphragm motor 7 of sample pump 7 is vented to the atmosphere through timing valve 9. The opening and closing of timing valve 9 under the ultimate direction of timer 11 activates the sampling process that samples the natural gas presented from inlet pipe 2 and passes the samples to a sample cylinder 14 through sample cylinder pipe 13.

Sample pump 3 takes a small portion of natural gas from inlet pipe 2 and, when activated by the opening of timing valve 9, moves that small sample from sample pump 3 through sample cylinder pipe 13 to sample cylinder 14. Sample cylinder 14 then contains the accumulation of samples taken from the natural gas pipeline. Sample cylinder 14 may be removed and taken to a laboratory where its contents can be analyzed for the Btu content which, as discussed above, affects the price of the natural gas.

Figure 2:
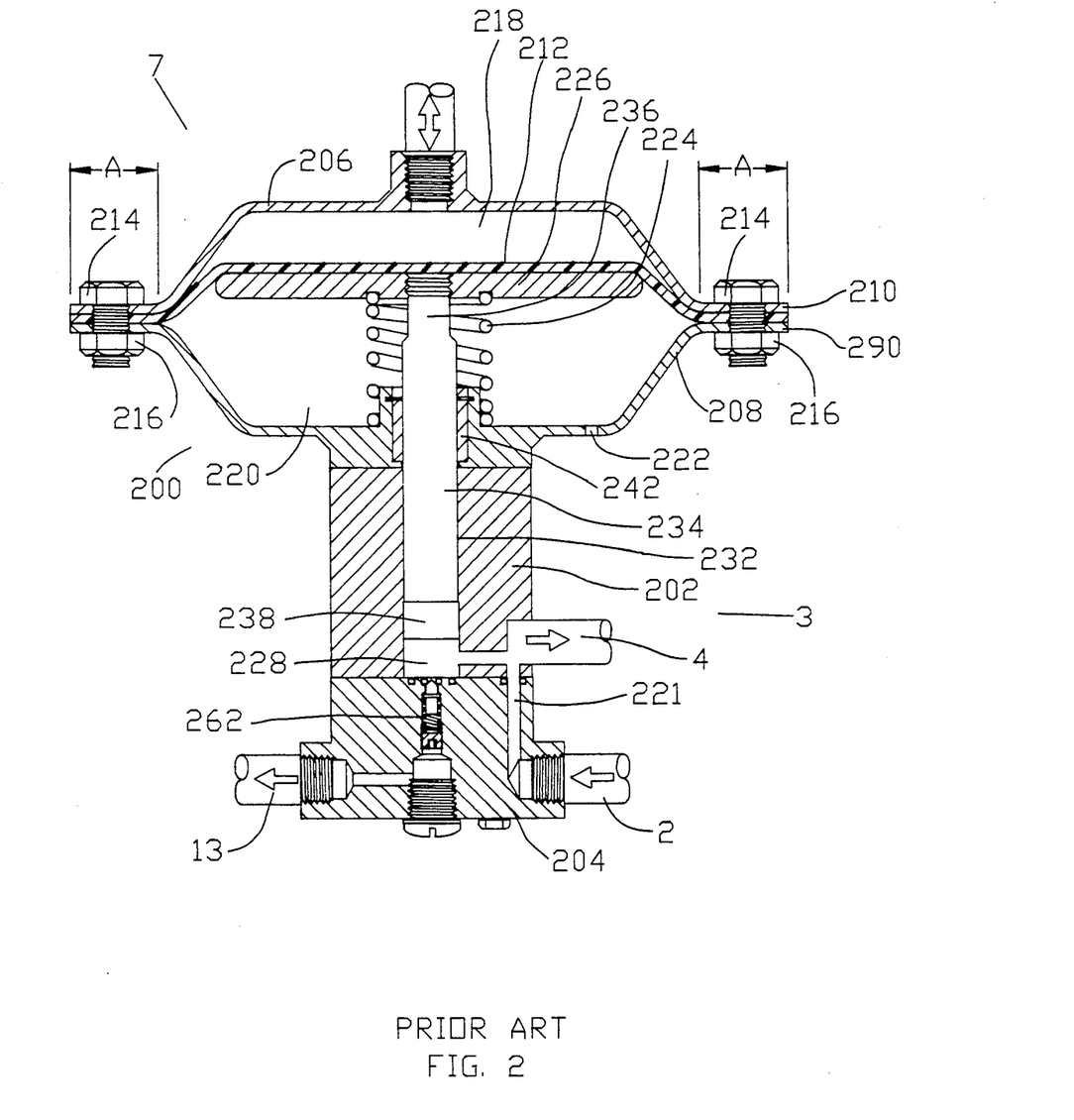
FIG. 2 is a schematic cross-sectional view of a typical prior art sampler pump.

A typical prior art sample pump 3 sold by the Welker Engineering Company as model GSS-4 is shown in schematic cross section in FIG. 2. The sample pump 3 shown in FIG. 2 contains a diaphragm case 200 that is attached to sample pump pipe 12. A body 202 is attached to diaphragm case 200 opposite sample pump pipe 12. Body 202 is in turn connected to manifold 204 opposite diaphragm case 200.

Diaphragm case 200 contains two parts, a pressure chamber cover 206 and an ambient atmosphere chamber cover 208. Pressure chamber cover 206 and an ambient atmosphere chamber cover 208 are both usually substantially bowl shaped and each has an annular outward projecting flange 210 that extends away from the edge of the covers 206, 208 at substantially a right angle to the central axes of the covers 206, 208. Covers 206, 208 are placed in contact with each other at flange 210.

A flexible gas tight diaphragm 212 is placed between the respective flanges 210 of covers 206, 208 as covers 206, 208 are brought into contact with each other along the respective flanges 210. A series of bolts 214 and nuts 216 extend through holes in flange 210 located at equally spaced locations around the periphery of covers 206, 208. The plurality of bolts 214 and nuts 216 combine to bring both sides of covers 206, 208 into tight contact with each other and diaphragm 212 to form a gas tight seal between diaphragm 212 and the ambient atmosphere at flange 210.

A typical prior art sample pump will have about eighteen (18) bolts 214 and nuts 216 holding covers 206, 208 together. When covers 206, 208 are to be joined in assembling or servicing the sample pumps, flanges 210 on covers 206, 208 are abutted and each of the eighteen bolts must be passed through an aligned hole in each flange 210 of cover 206, 208. In addition, the bolt 214 will also preferably pass through a hole in diaphragm 212 corresponding to the holes positioned in the flanges 210. Thereafter, each bolt 214 has a nut 216 placed on its end that is rotated by a wrench until it is tightened. During this process, it is easy for the bolts or nuts to become dropped or misplaced. This is clearly a problem to be avoided.

An additional problem related to this flange and nut and bolt joining system is that if a single bolt 214 and its corresponding nut 216 are not securely tightened, the gas tight seal at that point may be broken. As will be explained hereafter, it is important to the operation of sample pump 3 that a gas tight seal be maintained around flange 210.

A further problem with the bolt and nut connection system of the prior art sample pumps described above is that a wrench is required to disassemble and reassemble the diaphragm case 200 of the sample pumps 3. Often a wrench to fit the bolts 214 and nuts 216 is difficult to locate or unavailable. Also, during the disassembly and reassembly process the wrench may be dropped or misplaced. Clearly, it is desirable to eliminate the need to have to use a wrench to assemble or disassemble a sample pump.

A gas tight pressure chamber 218 is formed between pressure chamber cover 206 and diaphragm 212. Because pressure chamber 218 is gas tight and in fluid communication with sample pump pipe 12, the pressure in sample pump pipe 12 will be the pressure in pressure chamber 218.

An ambient atmosphere chamber 220 is formed between ambient atmosphere chamber cover 208 and diaphragm 212. A vent 222 connects ambient atmosphere chamber 220 and ambient atmospheric pressure so that air within ambient atmosphere chamber 220 is at the ambient atmosphere pressure.

A planar metal plate 226 abuts diaphragm 212. A spring 224 is placed within ambient atmosphere chamber 220 between ambient atmosphere chamber cover 208 and plate 226. Spring 224 biases plate 226 into contact with diaphragm 212 and aligns plate 226, in spring 224's unstressed configuration, with the plane formed through flanges 210 when covers 206, 208 are connected by bolts 214 and nuts 216.

Base 204 is fluidly connected to and communicates both with inlet pipe 2 and sample cylinder pipe 13 as described above. Some natural gas entering sampler pump 3 through inlet pipe 2 passes through connecting passageway 221 to outlet pipe 4 where it passes to regulator/relief valve 5 as described above. Some of the natural gas passes to a sample chamber 228 in body 202.

As described above, some natural gas leaving sample pump 3 through outlet pipe 4 eventually enters pressure chamber 218 through sample pump pipe 12 when timing valve 9 is opened under the direction of timer 11. When timing valve 9 is opened, natural gas passes through timing valve 9 into pressure chamber 218 of diaphragm case 200 to activate the diaphragm motor 7. In the chamber 218, the natural gas contacts diaphragm 212 that provides a gas tight barrier across diaphragm case 200. The pressure of the natural gas against diaphragm 212 causes diaphragm 212 to contact plate 226 and move both itself and plate 226 away from sample pump pipe 12 against the bias of spring 224.

Figure 3:
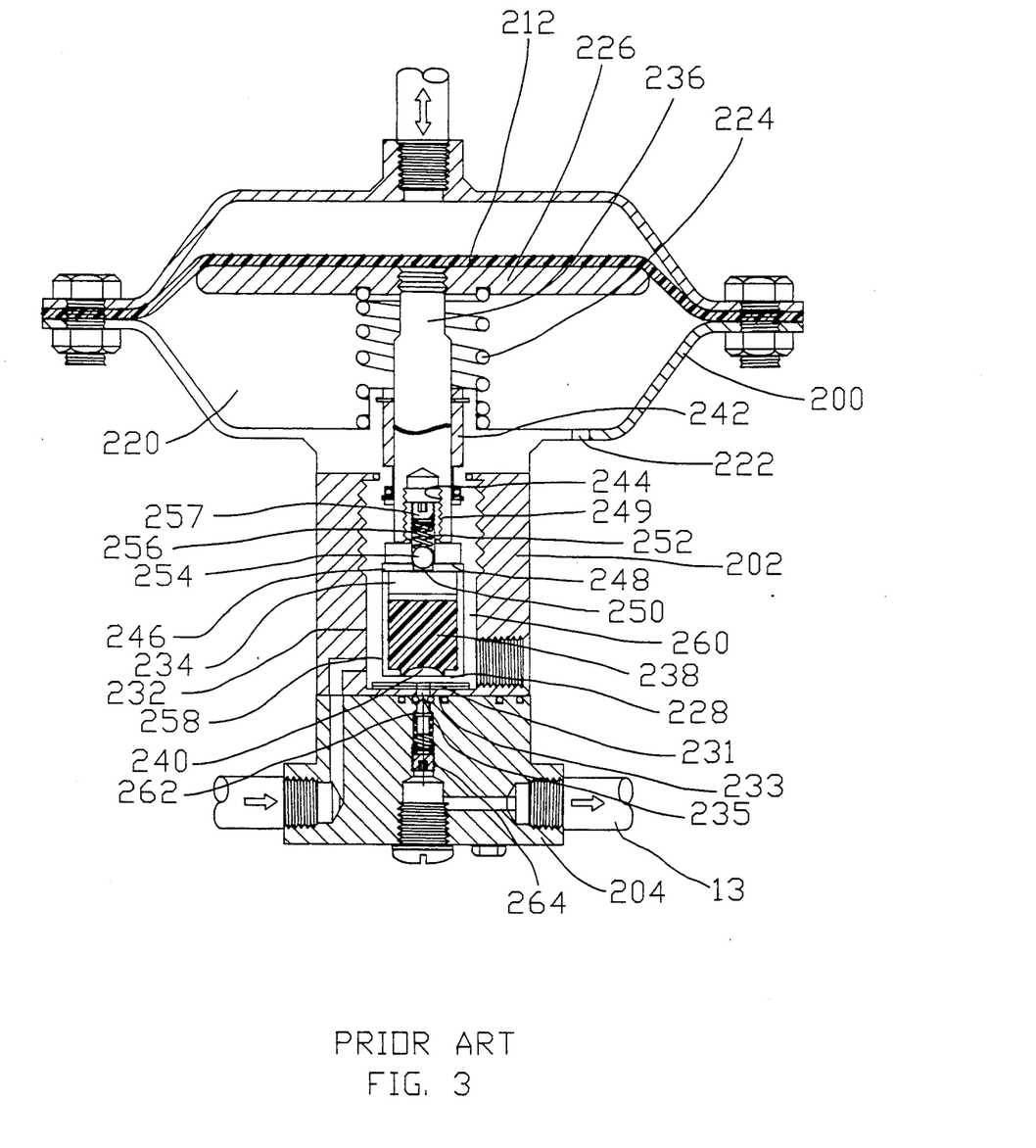
FIG. 3 is a detailed cross-sectional view of the body of the prior art sample pump of FIG. 2.

Referring to FIG. 3, body 202 contains a hollow cylinder 232 that is open at one end and substantially closed at the other. A sample chamber 228, as will be described in detail hereafter, is formed at the substantially closed end of cylinder 232.

A piston 234 is placed in hollow cylinder 232. An elongated piston rod 236 connects plate 226 to piston 234. Piston 234 is cylindrical, usually having a diameter larger than the diameter of piston rod 236 but slightly smaller than the diameter of hollow cylinder 232. Piston 234 moves within cylinder 232 and abuts a cylindrical elastomeric plug 238 having a diameter about equal to the diameter of piston 234. Plug 238 has a concave depression 240 opposite piston 234.

A gas tight seal 242 is placed around piston 234 within cylinder 232 so that gas within cylinder 232 cannot move out of the open end of cylinder 232 between piston 234 and cylinder 232 past seal 242.

In the prior art device described above, the piston 234 extends into a recess 244 in piston rod 236. Piston rod 236 is connected to the piston 234 by corresponding threads on piston 234 and recess 244. A pin 246 extends through a bore 248 located along the diameter of piston 234. Pin 246 is slightly longer than the diameter of piston 234 and contains a detent 250 at its midpoint. Bore 248 has a recess 252 extending away from bore 248 at a right angle at the midpoint of bore 248 in the neck 249 of piston 234.

A small metal ball 254 is located in recess 252 so that ball 254 extends into bore 248. A small spring 256 is located behind ball 254 in recess 252 to bias ball 254 into bore 248. A threaded stop 257 threadably engages threaded recess 252 to hold the spring 256 and ball 254 in place. When pin 246 is placed through bore 248 until it is centered in bore 248, ball 254 engages the detent 250 in pin 246 to hold pin 246 in position within bore 248.

A shield 258 extends around piston 234 and plug 238 and encases the end of plug 238 opposite piston 234. When pin 246 is in place in bore 248 the ends of pin 246 extend beyond the outer surface of piston 234 into elongated small holes 260 in shield 258. Holes 260 are elongated in the direction of the axis of piston 234. When plug 238 is not compressed by piston 234, as will be described hereafter, the ends of pin 246 contact the edges of holes 260 furthest from concave depression 240. The interaction between holes 260 and pin 246 holds shield 258 in position around piston 234 and plug 238.

As will be explained hereafter, as plug 238 is compressed by piston 234, the ends of pin 246 move within holes 260 from the position farthest from concave depression 240 toward concave depression 240. Ultimately, as plug 238 continues to be compressed, the ends of pin 246 will contact the edge of holes 260 closest to concave depression 240, thereby stopping further compression of plug 238.

This system of attaching the piston rod 236 to the piston 234 has been found to be expensive to manufacture due to the small size of the parts and the intricate work needed to form and assemble the ball 254, the spring 256, the stop 257 and the pin 246. It is clearly desirable to simplify the connection between the plug 238 and the piston 234.

As plate 226 is moved against the bias of spring 224 by the natural gas pressure within pressure chamber 218, piston rod 236 moves piston 234 toward the closed end of cylinder 232. As piston 234 moves toward the closed end of cylinder 232, the concave depression 240 of plug 238 moves into sealing contact with vacuum breaker wafer 231. A kelk spider seal 233 is captured between the wafer 231 and the bottom of cylinder 232. A bore passes through the center of wafer 231 and seal 233 and is aligned with sample outlet 235 in the bottom of cylinder 232. Further movement of piston 234 toward the closed end of cylinder 232 compresses plug 238 and the concave depression 240 against the closed end of cylinder 232. Because the concave depression 240 of plug 238 is pressed into sealing contact with the closed end of cylinder 232 and because plug 238 is made of an elastomeric material, as piston 234 compresses plug 238, the concave depression 240 collapses. The natural gas sample contained in the concave depression 240 passes through the center bore of wafer 231 and seal 233 and exits the sample chamber 228 through sample outlet 235.

A one-way valve 262 is in fluid communication with sample chamber 228 at the closed end of cylinder 232 so that sample chamber 228 is connected through one-way valve 262 to a pipe 13 that leads to sample cylinder pipe 14. When the pressure in sample chamber 228 becomes sufficiently high to overcome the bias of one-way valve 262, the natural gas within conical depression 240 passes through one-way valve 262 and pipe 13 into sample cylinder 14.

When timer 11 directs solenoid 10 to cause timing valve 9 to close, the natural gas under pressure within pressure chamber 218 is vented to atmosphere through sample pump pipe 12 and timing valve 9. Under the bias of spring 224, plate 226 and diaphragm 212 move back to their normal unstressed positions. As plate 226 moves back to its unstressed position, piston rod 236 and piston 234 also move away from the closed end of cylinder 232.

As the piston 234 moves away from the closed end of cylinder 232, the compression of plug 238 is reduced. When the pressure in sample chamber 228 drops below the pressure required to open one-way valve 262, one-way valve 262 will close so that sample chamber 228 will be a sealed chamber in contact with the closed end of cylinder 232. Further movement of piston 234 away from the closed end of cylinder 232 causes conical depression 240 to move away from sealing contact with the closed end of cylinder 232 so that a new sample of natural gas from connecting pipe 2 enters sample chamber 228.

Sampling systems such as the sampler assembly 1 shown in FIG. 1 are typically located at the "exchange points" where companies buy and sell gas or at a "gathering station" where pipelines from several natural gas wells come together.

Traditionally, both "exchange points" and "gathering stations" have been located on land. However, in recent years more and more natural gas wells have been drilled by offshore drilling rigs that drill into natural gas reservoirs located below water. On offshore drilling platforms, everything related to the drilling operation and the housing of the workers must be contained on the drilling platform.

It typically costs more to build a relatively larger offshore drilling platform than a smaller one. Therefore, offshore drilling platforms are made as small as possible. As a result, space on an offshore drilling platform is a precious commodity. Consequently, it is desirable to make sampler systems as small as possible in order to avoid taking up unnecessary and costly space.

Although less of a problem on land, it is still desirable to make sampler systems as small as possible. This is because on land, as well as on offshore drilling platforms, smaller sampler systems take up less space in the meter sheds or other structures placed over the sampler systems to protect them from the elements and from tampering or damage. The smaller the sampler systems, the smaller the protective structures can be. Smaller protective structures typically cost less to build and transport. Therefore, it is desirable to minimize the size of the sampler systems on land as well as on offshore drilling platforms in order of minimize the cost of protecting the sampler systems.

An additional benefit of reducing the size of the sampler systems is that smaller size usually means less material is needed to make the sampler systems. Because less material is needed to make the sample assemblies, the cost of materials for a sampler assembly drops.

A benefit related to reducing the amount of material needed to make sampler systems is that the time required to machine and polish the smaller component parts is usually reduced. As a result, reducing the size of the sampler systems usually means a reduction in the time, and corresponding cost, of manufacturing the components of the sampler systems.

A further benefit of reducing the size of the sampler systems is that smaller sampler systems typically require less energy to power the sampler assembly during the sampling process than do relatively larger sampler systems. Typical prior art sampler systems get their power to perform the sampling operation from the pressurized natural gas from the pipeline that is being sampled. As a result of the sampling operation, the pressurized natural gas that has powered the sampling operation is vented from the sampler assembly. Typically, the amount of natural gas released per sample is about 0.1 cubic feet.

Government regulations are now reducing the amount of, and in some cases forbidding, the release of natural gas into the atmosphere. As a result, the natural gas that previously was released into the atmosphere must now be collected or otherwise disposed of. One way of disposing of the previously released natural gas is to burn the gas in a catalatic heater. Whether collecting the previously released natural gas or alternately disposing of it, it is desirable to minimize the amount of natural gas released from the sampler assembly. Reducing the size of the sampler systems usually results in smaller amounts of natural gas being expelled from the sampler systems during the sampler process. Smaller amounts of natural gas released from the sampler systems translates into less cost for disposing of the released natural gas. In contrast with the prior art, the present miniaturized sampler vents only approximately 0.005 cubic feet of natural gas per sample.

Besides the disadvantages of taking up increased space, costing more to shelter and more to make, and reducing the amount of natural gas released from the sampler systems, another reason to make sampler systems as small as possible, particularly as it relates to offshore drilling platforms, is to minimize the difficulty involved in transporting relatively large components of the sampler assembly to and from the sampler assembly. For example, a typical prior art sample pump alone is typically about $8\frac{1}{2}'' \times 8\frac{1}{2}''$ and weighs about $12\frac{1}{2}$ pounds. Often, transporting such a pump to an offshore drilling platform in a helicopter requires that an entire passenger seat be used to carry the sample pump. This means that in a typical four-passenger helicopter, only three passengers and a sample pump may be transported at one time. In such circumstances, it is clearly desirable to minimize the size of the individual components of the sampler assembly, particularly the sample pump to minimize the difficulty presented in transporting the pump. In contrast with the prior art, the present miniaturized sampler weighs approximately two and one-fourth ($2\frac{1}{4}$) pounds and is about $4\frac{1}{2}'' \times 4\frac{1}{2}''$.

As mentioned above, it is desirable to minimize the size of the sample pump 3 as much as possible. In this regard, one problem with the prior art pump shown in FIG. 2 is that flange 210 extends away from the main body of the respective covers 206, 208 by a significant distance, labeled "A" in FIG. 2. Since the function of flange 210 is to bind the two halves of covers 206, 208 together and form a gas tight seal, it is desirable to minimize the space needed to bind and seal the two sides of covers 206, 208 together in order to minimize the size of the sample pump 3.

SUMMARY OF THE INVENTION

A miniaturized sampler pump is disclosed for taking samples of natural gas from a natural gas pipeline and moving the samples to a means for storing the sampled natural gas. An elastomeric plug with a concave face reciprocates in a sample chamber. During the sampling process, the concave face is collapsed, transferring the entrapped gas to a sample cylinder. When the concave face relaxes and returns to its normal shape, a fresh sample of the natural gas enters the concave face. The device also includes a diaphragm motor and piston assembly for compressing the elastomeric plug or collection head. In the instant invention, the diaphragm motor is enclosed in a diaphragm case formed by two concentric cylindrical covers. Each cover is open at one end and substantially closed at the other end. The outer diameter of one of the covers is approximately equal to the inner diameter of the other cover. In addition, the cover of smaller diameter has threads located on its outer circumference while the cover of larger diameter has corresponding threads on its inner circumference. The larger diameter cover has a annular inner surface spaced a distance from its closed end. A flexible gas tight diaphragm is placed across this annular surface.

The two covers are aligned along their cylindrical axes and concentrically joined at their open ends by intermeshing the threads on the outer circumference of the cover of smaller diameter with the corresponding threads on the inner circumference of the larger diameter cover. The covers threadably engage each other. O-rings on both the larger and smaller diameter covers concentric with the annular surface provide a gas tight seal between the diaphragm and the larger and smaller diameter surfaces.

The device also contains a base for connecting the sample pump to the pipes transporting the natural ga from the natural gas pipeline and for connecting the sample pump to the pipes connecting the sample pump with the sample cylinder.

The instant invention includes a piston assembly having an improved means for connecting the piston to the piston rod. A pin, having a length longer than the diameter of the piston, is placed through the piston. A shield surrounds a portion of the piston and collection head and has a pair of holes corresponding in location to the end of the pin where it is in position through the piston. A ring encircles the shield over the holes and prevents the pin from moving out of position.

It is therefore a primary object of the instant invention to provide a sample pump that collects samples of natural gas from a source of natural gas, such as a natural gas pipeline, and passes the samples of natural gas to a sample cylinder.

It is another object of the instant invention to provide a sample pump which is smaller and more lightweight than prior art pumps.

It is another object of the instant invention to provide a sample pump that, on each pumping cycle, passes a sample of natural gas purely representative of the natural gas presented to the sample pump at that time.

It is another object of the instant invention to provide a sample pump that is economical and easy to make, operate and repair.

It is yet another object of the instant invention to provide a sample pump that receives its power for collecting natural gas samples from the natural gas pressure in the pipe connecting the natural gas pipeline to the sample pump.

It is another object of the instant invention to provide a sample pump that does not require a wrench to assemble and service the diaphragm motor.

It is another object of the instant invention to provide a sample pump that provides a continuous seal around the periphery of the diaphragm.

These and other objects of the instant invention will be clear from the description contained herein and more particularly with reference to the attached drawings or similar elements that are referred to by similar reference numbers.

DETAILED DESCRIPTION OF THE INVENTION

Figure 4:
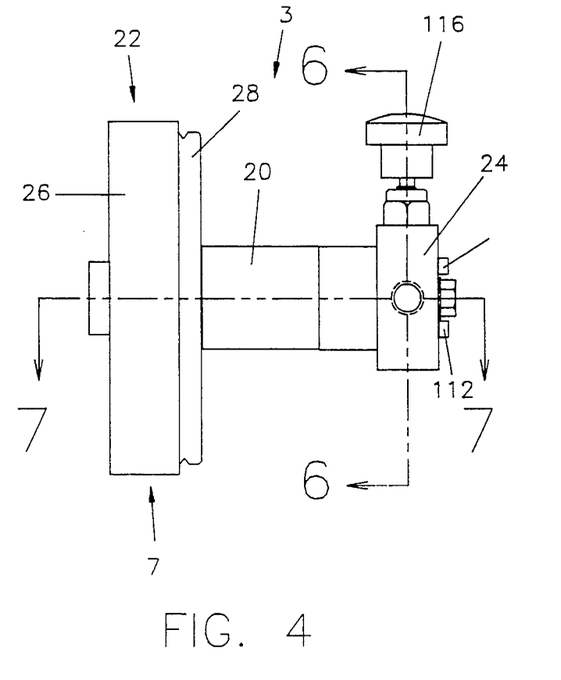
FIG. 4 is a side elevational view of the instant invention.
Figure 5:
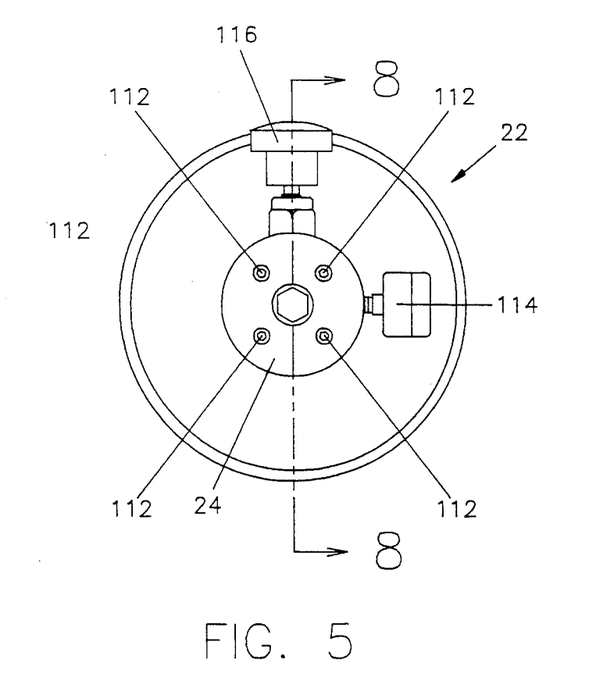
FIG. 5 is an end view of the sampler pump of FIG. 4.

Referring to FIG. 4, the sample pump of the instant invention, generally labeled 3, is disclosed. Sample pump 3 includes a generally cylindrical body 20 connected at one end to a diaphragm motor 7 and at the other end to a base 24.

Figure 7:
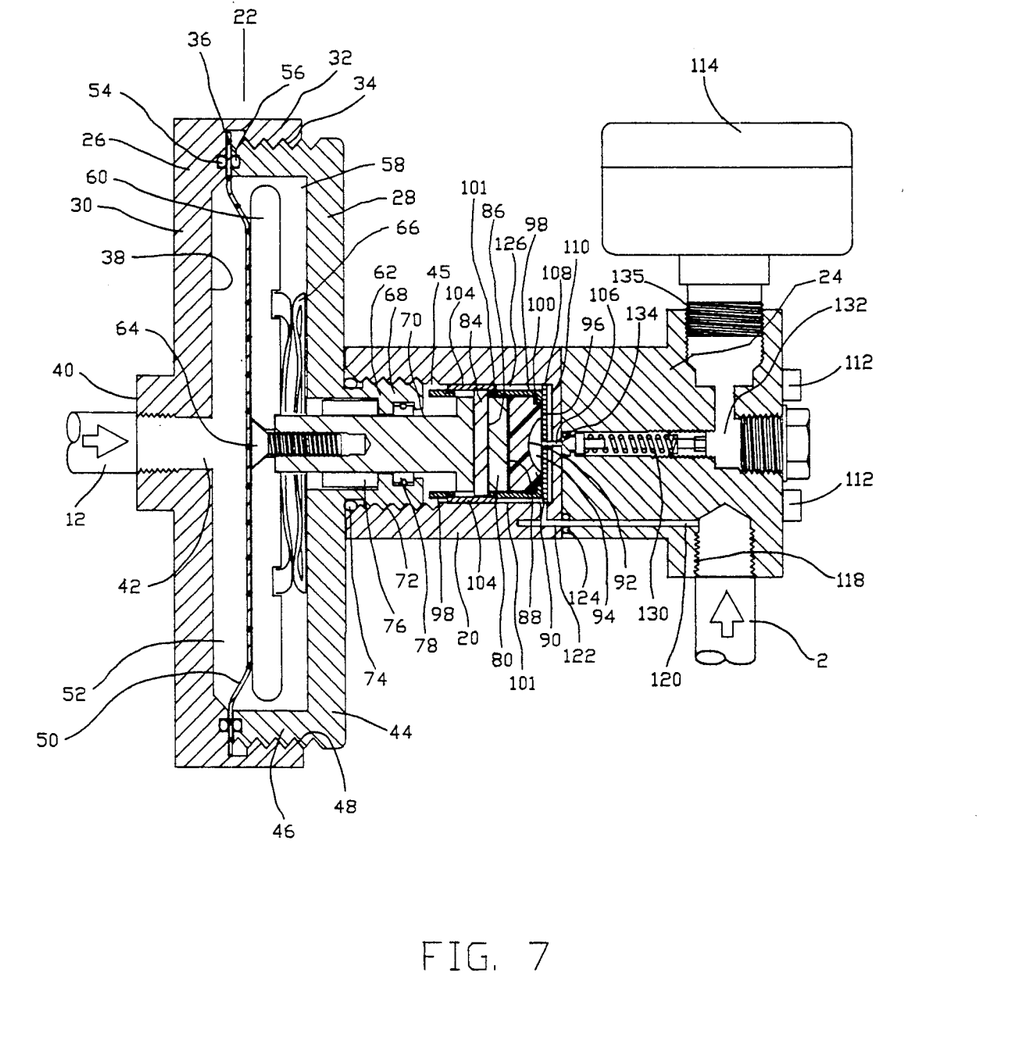
FIG. 7 is a cross-sectional view of the sampler pump of FIG. 4 along the line labeled 7—7 in FIG. 4 and shows the instant invention in sample collection mode.

As best seen in FIGS. 4 and 7, diaphragm case 22 is made of an upper diaphragm case 26 and a lower case 28. Upper diaphragm case 26 is generally cylindrical and includes a substantially planar upper diaphragm face 30 and an upper diaphragm lip 32 extending away from upper diaphragm face 30 at substantially a right angle. Upper diaphragm lip 32 contains threads 34 on its inner circumference. An annular flat 36 extends around the inside edge of upper diaphragm lip 32 a distance away from the inside surface 38 of upper diaphragm face 30.

Upper diaphragm case 26 also includes a connecting pipe connector 40 attached to upper diaphragm face 30. Connecting pipe connector 40 contains a central passage 42 having internal threads that extends through upper diaphragm face 30 and allows upper diaphragm case 26 to be connected to sample pump pipe 12.

Lower diaphragm case 28 contains a substantially planar lower diaphragm face 44. Lower diaphragm sides 46 extend away from lower diaphragm face 44 at substantially a right angle. Lower diaphragm side 46 has threads 48 on its outer circumference which threadably engage threads 34 on upper diaphragm lip 32. Lower diaphragm face 28 is sized so that when upper and lower diaphragm cases 26 and 28 are aligned along their cylindrical axes and brought into contact, threads 48 mesh concentrically with threads 34 upon rotation of lower diaphragm 28 relative to upper diaphragm case 26.

A flexible, gas tight, substantially circular diaphragm 50 is positioned across diaphragm case 22 between upper and lower diaphragm cases 26 and 28. The diameter of diaphragm 50 is preferably about equal to the diameter of upper diaphragm case 26. Diaphragm 50 is positioned on annular flat 36 extending around the inside edge of upper diaphragm lip 32. In this way, an upper diaphragm chamber 52 is formed between diaphragm 50 and the inner surface 38 of upper diaphragm face 30.

An O-ring 54 is placed in a channel in flat 36 to come in contact with diaphragm 50. A corresponding O-ring 56 is placed in a channel in lower diaphragm side 46, opposite O-ring 54, so that when upper and lower diaphragm cases 26 and 28 are in threading connection, lower diaphragm side 46 will push O-rings 56 and 54 against diaphragm 50 and provide a gas tight seal around diaphragm 50.

Figure 8:
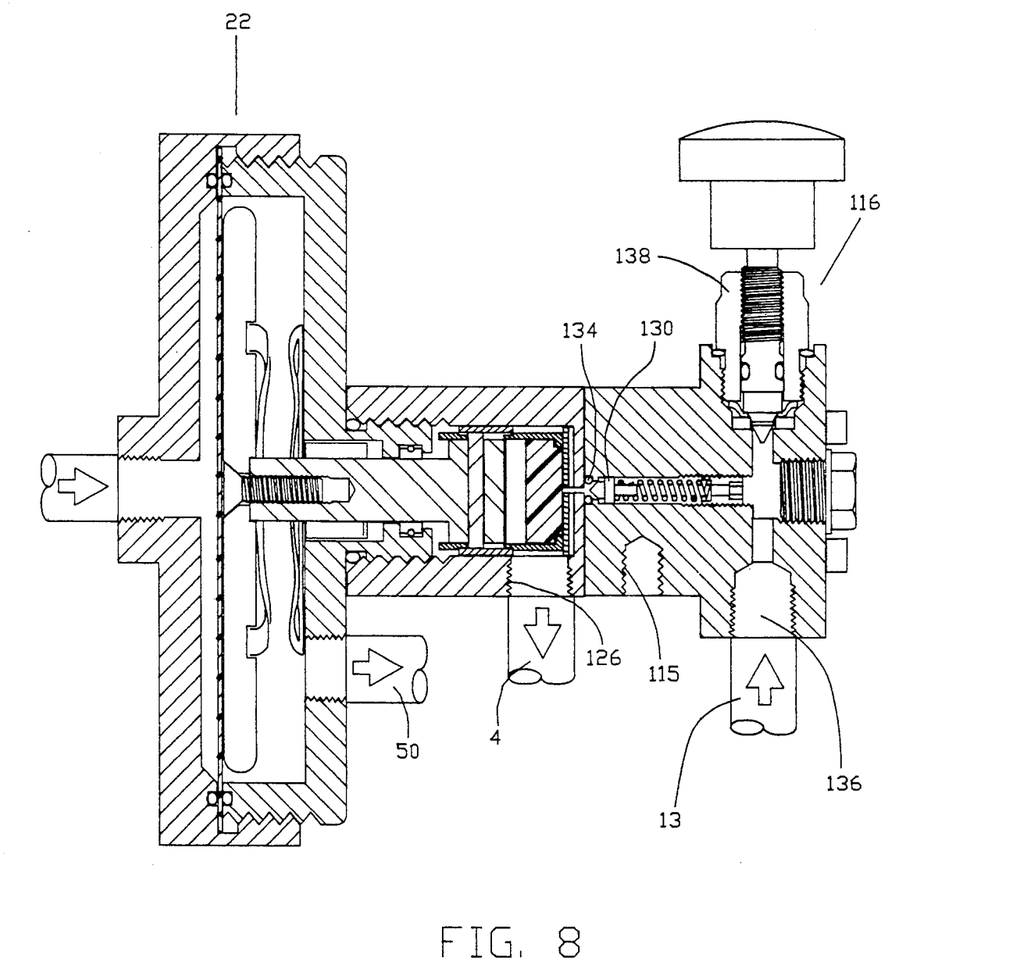
FIG. 8 is a cross-sectional view similar to FIG. 7 with the sampler device of FIG. 4 in its sample passing mode.
Figure 9:
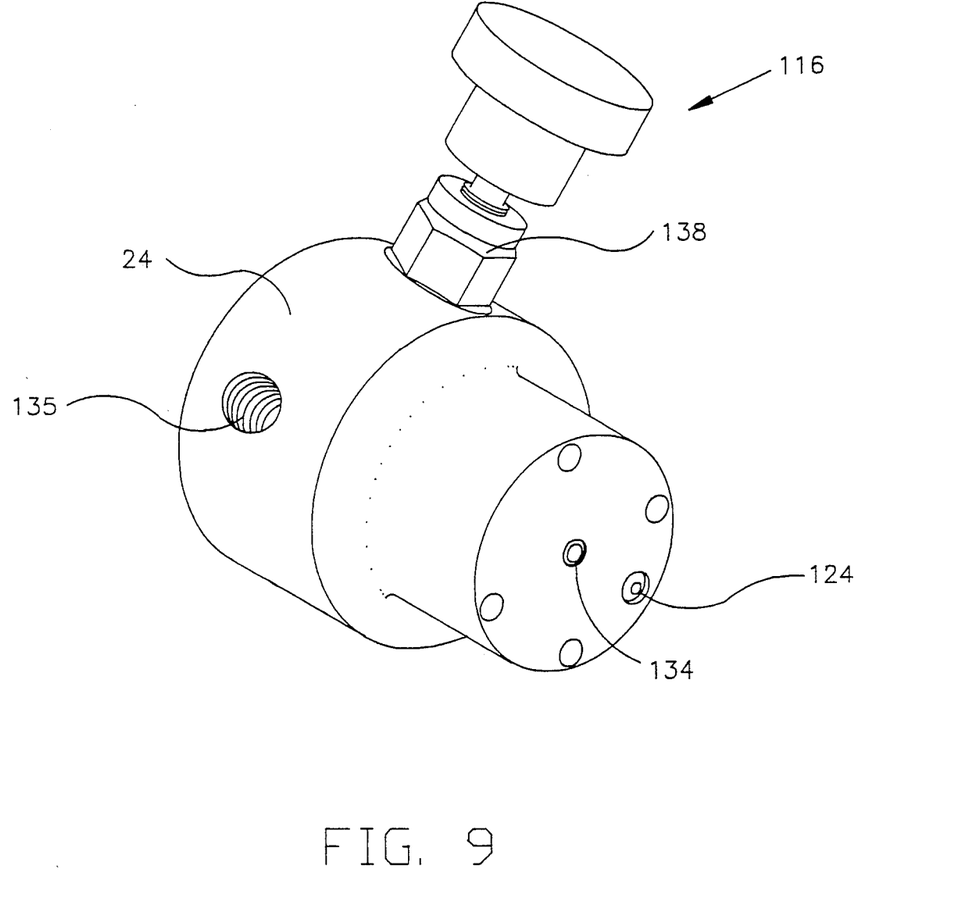
FIG. 9 is a perspective view of the base of the instant invention.
Figure 10:
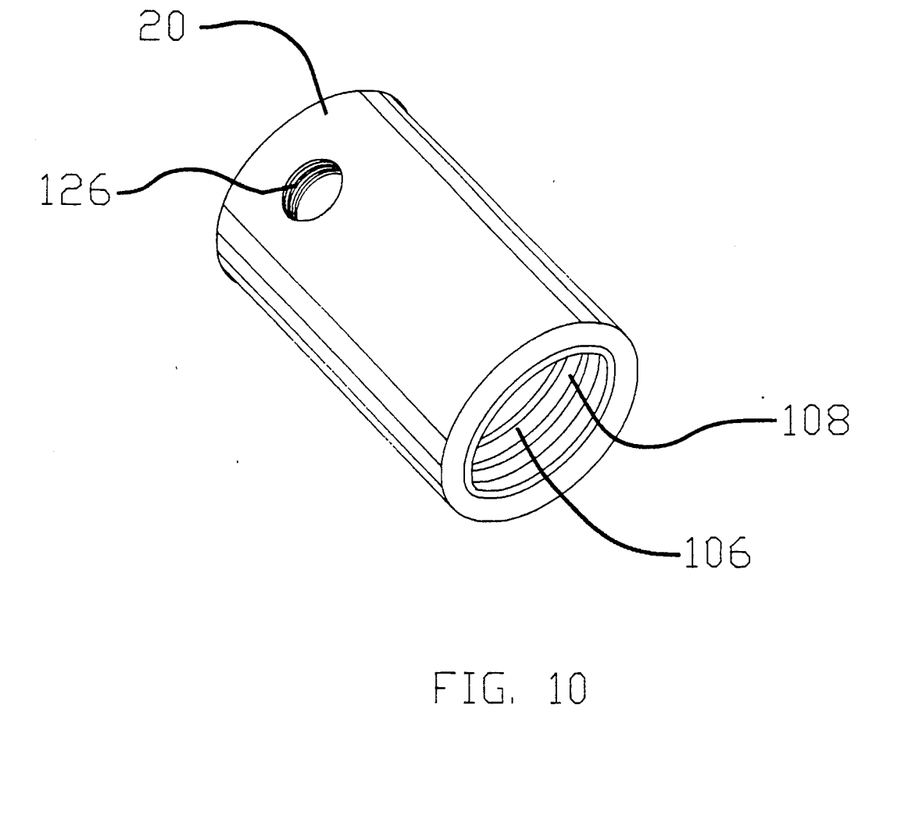
FIG. 10 is an end view, as viewed from the diaphragm case, the body of the instant invention.

A lower diaphragm chamber 58 is formed between diaphragm 50 and lower diaphragm face 44. O-rings 54 and 56, in contact with diaphragm 50, forms a gas tight chamber in upper diaphragm chamber 52. A vent 50 extends through lower diaphragm face 44 and connects lower diaphragm chamber 58 with the ambient atmosphere (FIG. 8).

A planar circular plate 60 is placed within lower diaphragm chamber 58 in contact with and parallel to diaphragm 50. Plate 60 is removably connected to piston shaft 62, which extends away from plate 60 at a right angle, by screw 64 which passes through plate 60 into piston shaft 62.

A wave spring 66 is placed within lower diaphragm chamber 58 between plate 60 and lower diaphragm face 44. Spring 66 biases plate 60 in contact with diaphragm 50 when diaphragm 50 is in an unstressed condition within diaphragm case 22.

A substantially cylindrical neck 68 extends away from lower diaphragm face 44. The outer surface of neck 68 has exterior threads 72 which intermesh with corresponding threads on the inner surface cylinder 45 in body 20. Neck 68 is screwed into cylinder 45 so that body 20 is brought into contact with the outer surface of lower diaphragm face 44. An O-ring 74 extends around the base of neck 68 and provides a seal between the neck 68 and body 20.

A bearing 76 is located in the bore 70 of neck 68. Bearing 76 has an inside diameter approximately equal to the outer diameter of piston shaft 62. Bearing 76 positions and allows piston shaft 62 to move along the elongated axis of piston shaft 62 as will be described hereafter.

A seal 78 is located in the bore 70 of neck 68 near the end of neck 68 farthest from lower diaphragm face 44. Seal 78 provides a gas tight seal between lower diaphragm chamber 58 and sample chamber 94.

As described above, piston shaft 62 is connected at one end to plate 60 by screw 64. An enlarge piston 80 extends from an forms a part of piston shaft 62 opposite screw 64. The surface of piston 80 opposite screw 64 is planar and perpendicular to the axis of piston shaft 62.

Both piston shaft 62 and piston 80 are cylindrical in cross section; the diameter of piston 80 being somewhat larger than the diameter of piston shaft 62. Piston shaft 62 is integrally formed from the same piece as piston 80. A pin 84 extends through a bore 86 located along the diameter of piston 80. Pin 84 is slightly longer than the diameter of piston 80.

The planar face of piston 80 contacts a disk 88 which in turn contacts a substantially cylindrical collection head 90. Collection head 90 is made of an elastomeric material and has a concave face 92 opposite piston 80. The collection head 90 is positioned in a sample chamber 94 in the lower end of cylinder 45. The collection head 90 reciprocates in the cylinder 45 in response to actuation of the diaphragm motor 7. When collection head 90 is relaxed, concave face 92 is open to sample chamber 94 and is filled with gas. When the diaphragm motor 7 actuates, it compresses collection head 90 against vacuum breaker wafer 108. This traps approximately 0.2 cubic centimeters of gas between the concave face 92 of collection head 90 and the wafer 108. Upon further compression of the collection head 90, the concave face 92 collapses and forces the entrapped ga into the sample cylinder 14 as will be more fully described hereinafter.

In the preferred embodiment, collection head 90 is about ½" in diameter and 9/32" long, although other dimensions will occur to those skilled in the art. The volume of liquid trapped by the concave face 92 and wafer 108 with this size collection head 90 is preferably 0.22 cubic centimeters but may vary from below 0.065 cubic centimeters to above 0.5 cubic centimeters.

The preferred durometer of collection head 90 is 70 but other durometers including but not limited to 80 and 90 may also be used.

A cylindrical shield 98 surrounds and encases both collection head 90 and piston 80. The inner diameter of shield 98 is about the same as the outer diameter of piston 80, disc 88 and collection head 90. Shield 98 also has an annular lip 100 at its end nearest the closed end of cylinder 45. Lip 100 extends inward from the main body of shield 98 and encases the end of collection head 90. Collection head extension 96 extends beyond the end of shield 98.

Shield 98 has a pair of opposed elongated pin receiving holes 101 to receive pin 84. Pin receiving holes 101 are elongated in the direction of the elongated axis of piston shaft 62. When pin 84 is in place in bore 86 the ends of pin 84 extend beyond the outer surface of piston 80 into holes 101 on opposite sides of shield 98. The interaction between holes 101 and pin 84 holds shield 98 and collection head 90 in position on piston 80.

Pin receiving holes 101 are positioned in shield 98 so that when pin 84 is placed through piston 80 and piston shaft 62, pin 84 extends beyond piston 80 into pin receiving holes 101 into contact with the end of pin receiving hole 101 opposite the closed end of cylinder 45. As will be described hereafter, as piston 80 pushes collection head 90 into contact with the closed end of cylinder 45, thereby compressing collection head 90, pin 84 will move with piston 80.

A ring 104 circles shield 98 and covers pin 84 so that pin 84 is held in position within the corresponding holes 101 of shield 98. When ring 104 is in position around shield 98, it has an outer diameter approximately equal to the diameter of cylinder 45. The ring 104 is circular to surround shield 98; however, ring 104 has a cut, not shown in the drawing, entirely through the ring 104. The cut allows the ring 104 to flex and to be easily slipped on and off the shield 98. The ring 104 is preferably formed from metal which can be repeatedly deformed and still return to an original configuration. When the ring 104 is removed from the shield 98, a screwdriver is typically inserted in the cut and the ring 10 is expanded to slip off the shield 98 to expose pin 84. Once removed, the ring 104 immediately returns to its original shape.

To put the ring 104 back on the shield, it must be manually expanded and slipped over shield 98 where it immediately returns to its original circular configuration, thus holding pin 84 in place. This ring 104 is more economical to produce than prior art arrangements and is easier to service than prior art arrangements.

As described above, neck 68 extends into cylinder 45 in body 20. Part of piston shaft 62 and the entirety of piston 80, disk 88, collection head 90, shield 98, pin 84 and pin ring 104 also extend into cylinder 45. A small sample outlet passage 106, aligned with the central axis of cylinder 45 connects sample chamber 94 with the exterior of body 20 as will be described hereafter.

A circular vacuum breaker wafer 108 and kelk spider seal 110 are positioned at the closed end of cylinder 45 in the sample chamber 94. Both vacuum breaker wafer 108 and kelk spider seal 110 have an outer diameter slightly less than the inner diameter of cylinder 45. The vacuum breaker wafer 108 has a small hole passing entirely through the wafer aligned with the central axis of cylinder 45. The kelk spider seal 110 has a small hole 113 entirely through the seal aligned with the central axis of the cylinder 45. These small holes are aligned with the sample outlet passage 106.

As previously mentioned, the vacuum breaker wafer 108 and the kelk spider seal 110 are positioned at the bottom of the cylinder 45. When the plug 90 is fully compressed the concave face 92 collapses against the vacuum breaker wafer 108. The kelk spider seal 110 is captured between the bottom of the cylinder 45 and the wafer 108. The wafer 108 provides a smooth surface to contact the plug 90. The kelk spider seal 110 provides a seal between the wafer 108 and the bottom of the cylinder 45 when the sample is being pumped from the concave face 92 through the sample outlet passage 106.

After the sample has passed from the concave face 92 to the sample cylinder, the plug 90 returns to a relaxed position. But for the wafer 108 and the seal 110 there would be a vacuum between the plug 90 and the bottom of the cylinder 45 which would make it difficult to return the plug 90 to a relaxed position. This vacuum would also tend to deform the plug 90.

Figure 11:
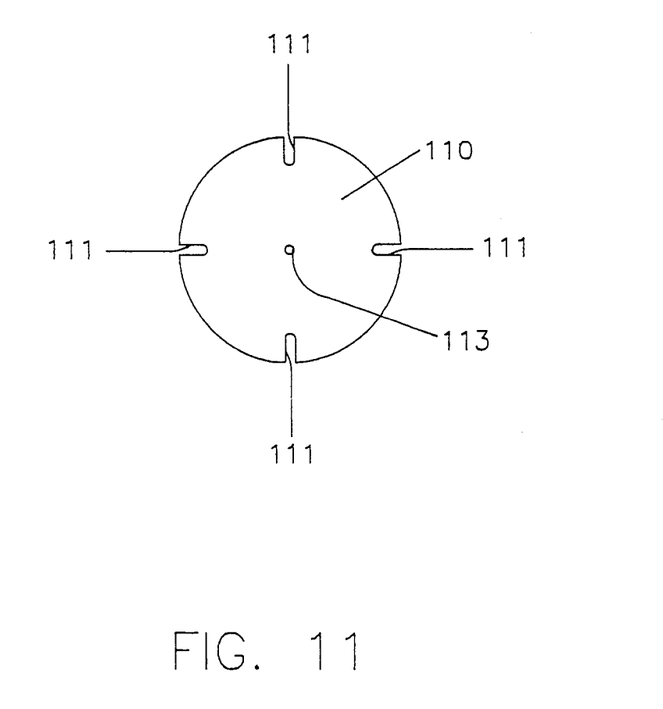
FIG. 11 is a top plan view of the kelk spider seal.

To overcome the vacuum, the kelk spider seal 110 has a plurality of radial notches 111 cut in the circumference, as better seen in FIG. 11. When the piston 80 begins to move away from the bottom of the cylinder 45, the plug 90 begins to relax and gas enters the radial notches 111 from the sample chamber 94 and breaks the vacuum between the plug 90, the wafer 108, the seal 110 and the bottom of the cylinder 45.

Body 20 is connected to base 24 by the means of a plurality of screw 112 extending from the end of base 24 opposite body 20 through base 24 into threaded recesses 142 (not shown) in body 20. When screws 112 are rotated, base 24 is brought into snug and secure contact with body 20.

Base 24 contains the connecting passageways connecting inlet pipe 2 with sample pump 3. In addition, base 24 connects sample pump 3 to sample pump cylinder pipe 13 as well as gauge 114 and bypass valve 116 as will be explained hereafter.

Figure 6:
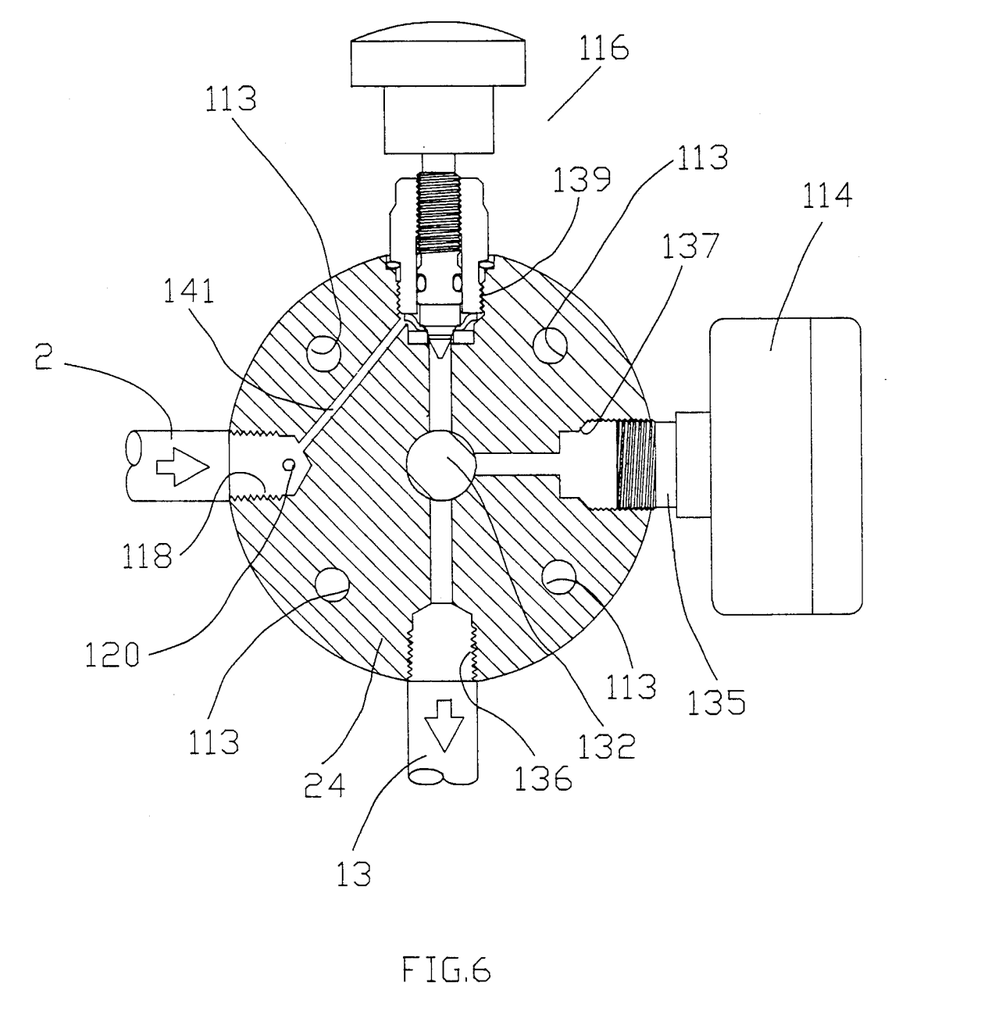
FIG. 6 is a cross-sectional view of the sampler pump of FIG. 4 along the line labeled 6—6 in FIG. 4.

FIG. 6 is a sectional view along line 6—6 of FIG. 4. The inlet port 118 is positioned at nine o'clock and receives the inlet pipe 2. Connecting passageway 120 is positioned at the bottom of inlet port 118. The sample outlet port 136 is positioned at six o'clock and receives sample outlet pipe 13. The gauge port 137 is positioned at three o'clock and receives the pressure gauge 114 which senses and reads pressure in distribution chamber 132. A purge valve port 139 receives a purge valve 116. A purge passageway 141 allows fluid communication between the inlet port 118 and the sample outlet port 136 when the purge valve 116 is open. The purge valve 116 is normally in the closed position during operation of the sampler 3. On occasion, when the sample cylinder 14 is charged and removed from the system, the operator will open purge valve 116 to blow gas through the inlet port 118 and sample outlet port 136 to clean out the passages to ensure a representative sample from the next sample cylinder.

The holes 113 allow screws 112 to pass through the base 24 and connect same to the body 20. A threaded receptacle 115 is formed in base 24. The receptacle 115 threadably receives a support, not shown, to mount the sampler 3 in a meter shed or other suitable location.

As can be seen in FIG. 7, inlet pipe 2 is connected to base 24 through inlet port 118. Connecting passageway 120 connects inlet port 118 and a sample chamber connecting passageway 122 leading to sample chamber 94. An O-ring 124 encircles connecting passageway 120 where it passes from base 24 to body 20 so that a gas tight seal is provided through this interface.

As better seen in FIG. 8, outlet port 126 is formed in cylinder 45 allowing fluid communication between inlet pipe 2 and outlet pipe 4 through sample chamber 94. Sample chamber connecting passageway 122 also provides fluid communication of natural gas from inlet pipe 2 to outlet port 126.

One-way valve 130 is aligned with and in fluid communication with sample outlet passage 106 in body 20. One-way valve 130 is a valve which opens only when exposed to pressures above a preselected pressure. One-way valve 130 is preferably a poppet valve but any other type of valve which opens at pressures above preselected pressure may be used as desired. One-way valve 130 connects sample outlet passage 106 with distribution chamber 132 located in base 24. An O-ring 134 encircles outlet passage 106 at the interface between body 20 and base 24 to provide an gas tight seal.

Distribution chamber 132 is in fluid communication with cylinder gauge 114 which is connected to base 24 through cylinder gauge connector 135. Distribution chamber 132 is also in fluid communication with sample outlet port connector 136 (FIG. 6).

OPERATION OF THE INVENTION

When the instant invention is in its relaxed position as shown in FIG. 7, natural gas enters base 24 through inlet pipe 2 at inlet port 118. From there, the gas passes through connecting passageway 120 to both sample chamber 94 and outlet port 126. From outlet port 126, natural gas passes to outlet pipe 4. The gas passing from inlet pipe 2 through collection chamber 94 and outlet pipe 4 is all at pipeline pressure.

As described above, regulator/relief valve 5 reduces the pipeline pressure to about 60-70 psi which then passes to timing valve 9. When timer 11 determines that it is appropriate to take a sample, timer 11 instructs solenoid 10 to open timing valve 9 thereby allowing natural gas under reduced pressure to pass through sample pump pipe 12 into upper diaphragm chamber 52 through connecting pipe connector 40. Because upper diaphragm chamber 52 is a sealed gas tight chamber, gas within upper diaphragm chamber 52 cannot escape. As described above, lower diaphragm chamber 58 is vented to the ambient atmosphere through vent 50. As a result, as gas flows into upper diaphragm chamber 52, the pressure within upper diaphragm chamber 52 will be at a greater pressure than the pressure within lower diaphragm chamber 58.

The increasing pressure within upper diaphragm chamber 52 causes diaphragm 50 to move away from upper diaphragm face 30 thereby contacting plate 60. As the pressure on plate 60 increases, the bias of spring 66 will be overcome thereby pushing plate 60 away from upper diaphragm face 30. As plate 60 moves away from upper diaphragm face 30, the movement of plate 60 will be transferred through piston shaft 62 to piston 80.

As plate 60 is moved toward base 24, piston shaft 62 is also moved toward base 24. Movement of piston 80 moves collection head 90 into contact with vacuum breaker wafer 108 located at the closed end of cylinder 45. Continued pressure on plate 60 causes piston shaft 62 to continue to move piston 80 toward lip 100, thereby moving the collection head 90 into contact with vacuum breaker 108. Because collection head 90 is made of an elastomeric material, as piston 80 compresses collection head 90, concave face 92 collapses. The gas that was trapped between the concave base 92 and the wafer 108 reaches a pressure that will open one-way valve 130, which allows the pressurized gas sample within to pass by one-way valve 130 into distribution chamber 132. FIG. 8 shows the collection head 90 in a fully collapsed position and the valve 130 in the open position to transfer a sample from the sample chamber 94 to the sample cylinder 14. Because distribution chamber 132 is in fluid communication with sample pump pipe 13 which is in turn connected to sample cylinder 14, the gas expelled from sample chamber 94 is stored in sample cylinder 14 for later analysis.

When timer 1 has determined that sufficient time has elapsed for collecting the sample, timer 11 directs solenoid 10 to close timing valve 9. This vents timing valve 9 to the ambient atmosphere. Because the gas pressure within upper diaphragm chamber 52 is pressurized, when timing valve 9 is opened, gas under pressure within upper diaphragm chamber 52 will leave upper diaphragm 52 through sample pump pipe 12 and escape from timing valve 9 into the ambient atmosphere.

As the pressure within upper diaphragm chamber 52 decreases, spring 66 gradually moves plate 60 back toward upper diaphragm case 26. As plate 60 moves toward upper diaphragm case 26, piston 80 is moved away from the bottom of the cylinder 45. Because natural gas under pressure is constantly present in connecting pipe 122, as the pressure on collection head 90 decreases, thereby allowing it to move out of sealing contact with vacuum breaker wafer 108, natural gas in connecting pipe 122 again enters sample chamber 94 through outlet port 126 and the space created between collection head 90 and vacuum breaker wafer 108. When the gas pressure within upper diaphragm chamber 52 is back to the ambient pressure, the sample pump 3 assumes the configuration shown in FIG. 7 and is in its relaxed position.

Because the volume of concave cavity 92 is reduced to virtually zero as piston 80 is moved under pressure from plate 60 towards base 24, virtually the entire natural gas sample trapped between the concave cavity 92 and the wafer 108 is passed through sample outlet passage 106 through one-way valve 130 each time the diaphragm motor 7 is activated. As a result, when plate 60 moves back to its non-stressed position, sample chamber 94 fills with an entirely new sample of natural gas, representative of the natural gas in the pipeline at that time.

The diaphragm case 22 described above having an upper diaphragm case 26 and a lower diaphragm case 28 forms a diaphragm case 22 without the protruding flange 210 and plurality of bolts found on the prior art devices.

In addition, the miniaturized diaphragm case described herein allows the diaphragm case 22 to be more easily serviced than the prior art diaphragm cases. In many prior art sample pumps, to separate the halves of the diaphragm case, a plurality of bolts 214 and nuts 216 have to be removed.

In the instant invention, upper diaphragm case 26 may be separated from lower diaphragm case 28 merely by hand rotating upper diaphragm case 26 relative to lower diaphragm case 28. To reconnect the upper and lower diaphragm cases 26 and 28, the two cases must merely be aligned and then upper diaphragm case 26 hand rotated relative to lower diaphragm case 28.

The thread connection of upper diaphragm case 26 and lower diaphragm case 28 allows cases 26 and 28 to be securely connected by hand pressure and without requiring a wrench. Further, the seal formed by O-rings 56 and 54 forms a continuous strong seal around the periphery of diaphragm 50. This seal does not have the problem of selective leaking around the periphery of diaphragm 212 that the prior art system of flange 210, bolt 214 and nut 216 connection has.

Further, because there are no bolts and nuts to hold the upper and lower diaphragm cases together, there is no chance of losing or misplacing the nuts and bolts that are required to connect upper and lower diaphragms in the prior art. This is particularly important in some environments where sample pumps are used, that is, perched high on offshore oil drilling platforms or within dark and cramped meter houses.

One further advantage of reducing the size of the diaphragm case is that when a sample pump must be placed outside of a meter house, and protected by a covering, the reduced size allows the protective covering to be reduced in size, thereby reducing the cost of the protective covering.

As mentioned above, it is desirable to reduce the size of the components of the sampler systems. The teachings of the instant invention allow sample pumps 3 to be made that are typically about 4¼" long and 4¼" across outer cover 206. Further, the weight of a typical sample pump 3 made according to the teachings of the instant invention is about 2 pounds 4 ounces. The teachings of the instant invention allow sample pumps 3 to be made that are significantly smaller in size and weight than are the prior art devices.

Further, the reduced size of the sample pump 3 made according to the teachings of the instant invention allows the cost of manufacturing sample pumps to be reduced to about ¼ to ½ the price of prior art pumps.

An additional advantage of the teachings of the instant invention allowing sample pumps 3 to be made smaller than the prior art devices is that the upper and lower diaphragm cases 26 and 28 may be machined in one piece in aluminum. This eliminates any welding of connecting pieces and the like that were required by the prior art devices with a corresponding reduction in manufacturing cost.

As mentioned above, gas that is expelled from sample pumps 3 during the sampling operation must be collected or otherwise disposed of. A sample pump made according to the teachings of the instant invention and made the size of the preferred embodiment will expel only about 0.005 cubic feet from the sample pump 3 during the sampling operation.

Although upper diaphragm case 26 and lower diaphragm case 28 have been described as having substantially planar faces 30 and 44, the substantially perpendicular sides 32 and 46, respectively, any other shape of upper and lower diaphragm cases 26 and 28 are within the scope of the invention so long as the respective upper and lower cases are attached concentrically along their outer edges. Further, although upper and lower diaphragm cases 26 and 28 have been described as connecting through intermeshing threads, other types of connection, as will occur to those skilled in the art, for concentrically attaching their respective sides 32 and 46, respectively, is within the scope of the invention.

Finally, although lower diaphragm case 28 has been described as having a smaller diameter so that it can be concentrically placed within upper diaphragm case 26, the reverse configuration may also be applied so that upper diaphragm case 26 may be sized to fit concentrically within lower diaphragm case 28.

It is within the scope of this invention to use a piston/cylinder arrangement in lieu of the diaphragm motor 7 as will be recognized by those skilled in the art.

The instant invention has been described in connection with a specific embodiment. However, it is to be understood that the description contained herein is for the purpose of illustration and not for the purpose of limitation. In particular, the dimensions given are not for the purpose of limiting the disclosure of the invention, but rather are illustrative of dimensions that have been found to be particularly useful in the art. Change and modifications may be made to the description contained herein and still be within the scope of the invention as claimed. Further, obvious changes and modifications will occur to those skilled in the art.

I claim:

1. A miniaturized natural gas sampler which pumps samples of natural gas from a pipeline into a sample cylinder comprising:

a diaphragm motor connected to a hollow body substantially closed at one end defining a sample chamber between said motor and said closed end, said body having an inlet passageway and an outlet passageway in communication with said sample chamber, said body connected to a base opposite said motor;

said base defining an inlet port and an intermediate inlet passageway in communication with said inlet port allowing fluid communication for the gas between the pipeline and said sample chamber via said inlet passageway, said base further defining a distribution chamber and an outlet port, allowing fluid communication for the gas between said sample chamber and the sample cylinder;

a one-way check valve positioned in said distribution chamber to isolate said sample chamber from said sample cylinder;

an elongate piston connected on one end to said diaphragm motor and the other end abutting an elastomeric collection head having a concave surface directed towards the closed end of said sample chamber, said piston and said collection head reciprocating to and fro in said collection chamber in response to actuation of said diaphragm motor to pump samples of natural gas from said sample chamber through said outlet passageway past said one way check valve into said distribution chamber and said outlet port to the sample cylinder;

said elongate piston having a bore near said collection head, said bore extending through said elongate piston perpendicular to the longitudinal axis of said elongate piston;

a hollow cylindrical elongate shield being open on both ends, said shield enclosing said collection head and having an annular lip directed inward from the outer surface of said shield at the end of said collection head opposite said piston, said shield having a recess encircling said outer surface, with a pair of opposed holes positioned in said recess, said holes passing through said shield; said shield extending around a portion of said piston at the end opposite said diaphragm motor;

a pin having a length longer than the diameter of said piston, said pin placed through said opposed holes in said shield and said bore in said piston to releasably attach said collection head and said shield to said piston;

a split ring extending around said shield to cover and hold said pin in place, said split ring sized and dimensioned to fit snugly in said recess encircling said outer surface of said shield; and said pair of opposed holes in said shield being elongated in a direction parallel to the axis of said piston, said pin contacting the end of said holes farthest from said collection head when said collection head is not compressed by said piston.

2. The sampler of claim 1 wherein said miniaturized sampler weighs less than 3 pounds.

3. The sampler of claim 1 wherein said diaphragm motor is actuated by approximately 0.005 cubic feet of gas per stroke of said piston.

4. The sampler of claim 1 wherein said collection head is approximately ½" in diameter and is approximately 9/32" long.

5. The sampler of claim 1 wherein said concave surface in said collection head pumps between 0.5 cc and 0.065 cc of gas per stroke of said piston.

6. A miniaturized natural gas sampler which pumps samples of natural gas from a pipeline into a sample cylinder comprising:

a motor housing connected to a hollow body substantially closed at one end defining a sample chamber between said motor housing and said closed end, said sample chamber in fluid communication with said pipeline and said sample cylinder;

a base having an inlet port and internal inlet passageways allowing fluid communication for the gas between the pipeline and said sample chamber, said base also having an outlet port and internal outlet passageways allowing fluid communication for the gas between said sample chamber and said sample cylinder;

a check valve means allowing gas to be pumped from said sample chamber into the sample cylinder, but preventing gas from flowing back from the sample cylinder into said sample chamber;

an elastomeric collection head positioned in said sample chamber to pump samples out of said sample chamber into said sample cylinder;

an elongate piston;

a motor means connected to one end of said elongate piston to stroke said piston to and fro in said sample chamber;

a shield encircling said collection head;

means for releasably attaching said collection head and said shield to said elongate piston on the end opposite from said motor means, said means for releasably attaching including a pin and split ring; and said miniaturized natural gas sampler weighing less than 3 pounds.

7. The sampler of claim 6 wherein said motor housing includes:

(a) a first substantially tubular cover having an open end and a substantially closed second end; and (b) a second substantially tubular cover having an open end and a substantially closed second end, said second cover having outer dimensions approximately equal to the inner dimensions of said first cover, said open end of said second cover placed concentrically within and threadably attached to said open end of said first cover.

8. The sampler of claim 7 wherein said motor means includes:

(a) a diaphragm in gas tight contact between said open end of said second cover and said open end of said first cover so that a high pressure chamber and a low pressure chamber is formed respectively between said closed end of said first cover and said diaphragm of said closed end of said second cover and said diaphragm;

(b) a circular plate positioned in said low pressure chamber and abutting said diaphragm, said plate connected to said piston, said plate and said piston moving to and fro in response to actuation of said diaphragm; and (c) at least one spring captured in said low pressure chamber between said plate and said closed end of said second tubular cover.

9. The sampler of claim 8 wherein said motor means is actuated by approximately 0.005 cubic feet of natural gas per stroke of said elongate piston.

* * * * *